(12) United States Patent
Poetzschke et al.

(10) Patent No.: US 10,646,507 B2
(45) Date of Patent: May 12, 2020

(54) COMPOSITIONS FOR IMPROVED TISSUE OXYGENATION BY PERITONEAL VENTILATION

(71) Applicants: Harald Poetzschke, Wiesbaden (DE); Hubertus Schmelz, Hamburg (DE)

(72) Inventors: Harald Poetzschke, Wiesbaden (DE); Hubertus Schmelz, Hamburg (DE)

(73) Assignee: Sangui BioTech International, Inc., Farmington, UT (US)

(*) Notice: Subject to any disclaimer, the term of this patent is extended or adjusted under 35 U.S.C. 154(b) by 74 days.

(21) Appl. No.: 14/469,846

(22) Filed: Aug. 27, 2014

(65) Prior Publication Data

US 2015/0064275 A1    Mar. 5, 2015

(30) Foreign Application Priority Data

Sep. 3, 2013   (DE) .................. 10 2013 014 651

(51) Int. Cl.
| | | |
|---|---|---|
| A61K 33/00 | (2006.01) | |
| A61K 38/42 | (2006.01) | |
| A61K 47/64 | (2017.01) | |

(52) U.S. Cl.
CPC ............. *A61K 33/00* (2013.01); *A61K 38/42* (2013.01); *A61K 47/6445* (2017.08)

(58) Field of Classification Search
None
See application file for complete search history.

(56) References Cited

U.S. PATENT DOCUMENTS

| | | | |
|---|---|---|---|
| 4,657,532 A | 4/1987 | Osterholm | |
| 4,963,130 A | 10/1990 | Osterholm | |
| 5,480,866 A * | 1/1996 | Bonaventura ......... | A61K 38/42 424/85.2 |
| 5,927,273 A * | 7/1999 | Federowicz ....... | A61M 16/0054 128/200.24 |
| 6,956,025 B2 | 10/2005 | Barnikol | |
| 7,005,414 B2 | 2/2006 | Barnikol et al. | |
| 2004/0023851 A1 * | 2/2004 | Barnikol ............... | A61K 38/42 530/385 |
| 2014/0010848 A1 * | 1/2014 | Kheir .................. | A61K 9/0019 424/400 |
| 2014/0316331 A1 * | 10/2014 | Borden ................ | A61M 1/28 604/26 |

FOREIGN PATENT DOCUMENTS

| | | | |
|---|---|---|---|
| DE | 100 31 742 A1 | 1/2002 | |
| DE | 100 31 744 A1 | 1/2002 | |
| DE | 100 31 740 A1 | 2/2002 | |
| EP | 0 209 128 A2 | 1/1987 | |
| EP | 2550973 A1 * | 1/2013 | ......... A61L 26/0076 |
| WO | 03/082392 A2 | 10/2003 | |
| WO | 03/094953 A1 | 11/2003 | |

OTHER PUBLICATIONS

Salomon, The Journal of General Physiology (1941), vol. 24, No. 3, pp. 367-375.*
Norman et al., Chochrane Database of Systematic Reviews, Issue 10. (Year: 2017).*
Matsutani et al., The Peritoneum as a Novel Oxygenation Organ: Revitalization of Intraperitoneal Oxygenation, Shock, 2008, pp. 250-253, vol. 30, No. 3.
Matsutani et al., Efficacy of Peritoneal Oxygenation Using a Novel Artificial Oxygen Carrier (TRM-645) in a Rat Respiratory Insufficiency Model, Surgery Today, 2010, 40, pp. 451-455.
Zhang et al., Effect of Oxygenation of Transperitoneal Ventilation on the Death Time After Asphyxiation in Rabbits, Minerva Anesthesiologica 2010; 76: pp. 913-918.
Jonathan B. Wittenberg ("The Molecular Mechanism of Hemoglobin-facilitated Oxygen Diffusion", Journal of Biological Chemistry 1966; 241: pp. 104-114.
Barr et al., "Peritoneal Ventilation: An Animal Model of Extrapulmonary Ventilation in Experimental Adult Respiratory Distress Syndrome", Pediatric Research 1994; 35: pp. 682-684.
Wang X et al., "The Effect of High and Conventional Frequency Peritoneal Jet Ventilation on Hypoxemia in ARDS Dogs", European Journal of Anaesthesiology 2012; 29: p. 180.

(Continued)

*Primary Examiner* — Hasan S Ahmed
(74) *Attorney, Agent, or Firm* — Collard & Roe, P.C.

(57) ABSTRACT

Compositions and methods for improving transperitoneal oxygen uptake during peritoneal ventilation for extrapulmonary oxygenation of an organism or individual organs in preferably life-threatening case of need, such as pulmonary failure or circulatory shock, are disclosed. Such deficiencies can be addressed by transperitoneal administration of oxygen via a gas introduced into the abdominal cavity. A liquid, preferably aqueous, composition including an oxygen carrier such as hemoglobin is used, which, surprisingly, is capable of increasing the effectiveness of the diffusion of the oxygen administered by a one-time or repeated filling or continuous flushing of the abdominal cavity. An oxygen carrier, such as hemoglobin or derivatives thereof, is used for the manufacture of a composition for improvement of the diffusion of oxygen (gas) introduced into mucus layers of the peritoneum, preferably to enhance the diffusion of oxygen in transperitoneal ventilation.

10 Claims, No Drawings

(56) References Cited

OTHER PUBLICATIONS

Giffin D.M., et al., "Oxygen Uptake During Peritoneal Ventilation in a Porcine Model of Hypoxemia", Critical Care Medicine 1998; 26: 1564-1568.
Printout article of "Mineral Processing and Extractive Metallurgy Review: An International Journal" downloaded date Nov. 20, 2014 (5 pages).
Printout Free Dictionary Website for the word ventilation (3 pages).
Communication under Rule 71(3) EPC with English translation dated Aug. 30, 2018 in European Patent Application No. 14 758 344.7-1112.

* cited by examiner

COMPOSITIONS FOR IMPROVED TISSUE OXYGENATION BY PERITONEAL VENTILATION

CROSS REFERENCE TO RELATED APPLICATIONS

Applicants claim priority under 35 U.S.C. § 119 of German Application No. DE 10 2013 014 651.8 filed Sep. 3, 2013, the disclosure of which is incorporated by reference.

BACKGROUND OF THE INVENTION

1. Field of the Invention

The present invention relates to the field of (trans)peritoneal ventilation of a mammal, preferably a human being, for additional oxygen supply to the organism or individual organs in case of preferably life-threatening need. This occurs in particular in case of insufficient supply of the blood and consequently the body with oxygen due to pulmonary failure. In addition, there can also be oxygen deficiency of individual abdominal organs, e. g. in case of circulatory shock (hypovolemic, septic, etc.). Such conditions can be managed by transperitoneal administration of oxygen from a gas introduced into the abdominal cavity (so-called peritoneal or transperitoneal ventilation), wherein according to the present invention additionally a liquid, preferably aqueous, composition comprising an oxygen carrier such as hemoglobin is used. Unexpectedly, such a liquid composition or solution comprising an oxygen carrier can increase the effectiveness of the diffusion of the oxygen administered by (one-time or repeated) filling or continuous rinsing of the abdominal cavity effectively and in a fast and easy way. This allows peritoneal ventilation to be improved and hypoxia in the body to be addressed more effectively.

The present invention insofar also relates to the presence or use of an oxygen carrier, preferably an oxygen carrier selected from hemoglobin, myoglobin, hemocyanin, erythrocruorin, or derivatives thereof, most preferably native porcine hemoglobin, especially having an oxygen half-saturation partial pressure between 1 and 50 mmHg, for the manufacture of a preferably aqueous composition for enhancement of the diffusion of oxygen (gas) introduced into mucous layers of the peritoneal mucosa, in particular in transperitoneal ventilation.

The invention further relates to a process for preparing a diffusion enhancer for improving oxygen supply of a mammal.

2. Description of the Related Art

In pulmonary failure—e. g. ALI (Acute Lung Injury) and ARDS (Acute Respiratory Distress Syndrome)—inter alia oxygen uptake and supply of the blood with fresh oxygen (oxygenation of the blood) are impaired. This leads to oxygen deficiency in the blood (hypoxemia) and subsequently in the body (systemic hypoxia, insufficient oxygenation of the tissues). For prevention of injury and eventually death, the affected subject must be therapeutically supplied with oxygen. In mild cases, it may suffice to increase the oxygen content in the respiratory air; in more severe cases, ventilation with (end-expiratory) overpressure can also be used. As an ultimate measure, the subject's blood can be loaded with oxygen (oxygenated) outside the body in a mechanical device (oxygenator). Technical oxygenators (e. g. extracorporeal membrane oxygenators, ECMOs) are used also during surgery, e. g. on the heart or the lungs (e. g. in the context of a so-called heart-lung machine). Their use is very complex and demanding, as well as very risky.

Moreover, there are medical conditions that are associated with reduced oxygenation of the organs in the abdominal cavity, i. e. local hypoxia, such as hypovolemic or septic circulatory shock, intestinal infarction, etc., as well as such as require temporary therapeutic increase of oxygenation of organs in the abdominal cavity (e. g. implantation of insulin-producing Langerhans cells into the liver, etc.), in which local improvement in oxygenation is medically desirable.

Various attempts have been made to develop new workable methods to overcome systemic or local hypoxia, in particular to avoid risks and obviate the need for elaborate technical devices, which may be unavailable in case of need. Thus, as an alternative method of non-pulmonary respiratory support, therapeutic oxygen supply via the mucous membrane of the abdominal cavity (the peritoneum, a serosa) has been considered.

A principal approach to (trans)peritoneal oxygenation is one-time or repeated filling or continuous rinsing of the abdominal cavity with an oxygen-rich liquid (comprising already dissolved oxygen). Appropriate compositions are or comprise e. g. oxygen-supersaturated aqueous salt solutions, or, preferably, also oxygenated (per)fluorocarbons. U.S. Pat. Nos. 4,657,532 and 4,963,130 as well as EP 0 209 128 B1 describe such a method of filling the abdominal cavity with oxygenated liquid fluorocarbon compounds or emulsion compositions comprising the same.

Another method is the use of oxygen-comprising gas in the form of peritoneal ventilation. This has been described e. g. by Zhang J.-Y., et al. in "Effect of Oxygenation of Transperitoneal Ventilation on the Death Time After Asphyxiation in Rabbits", *Minerva Anesthesiologica* 2010; 76: 913-918 by way of an experiment in rabbits, where detectable amounts of oxygen entered the animals' bodies (significantly prolonging their survival times).

In contrast to this, Giffin D. M., et al. report in "Oxygen Uptake during Peritoneal Ventilation in a Porcine Model of Hypoxemia", *Critical Care Medicine* 1998; 26: 1564-1568, using an anesthetized pig model, that in these larger organisms no significant increase in oxygen uptake is achieved by peritoneal ventilation.

None of the experimental methods listed has made it to clinical application readiness. Due to the different and sometimes contradictory results, no general method can be derived from these either.

SUMMARY OF THE INVENTION

The problem underlying the present invention is the need for medical improvement of hypoxic conditions of organisms (in particular mammalian organisms) or individual organs of the same in a simple and effective manner by (trans)peritoneal ventilation. Here the clinical benefits should clearly outweigh the risks, and the need for elaborate technology be obviated.

According to the present invention, this objective is achieved by application of (trans)peritoneal ventilation with an oxygen-comprising gas under concomitant application of a liquid composition comprising an oxygen carrier, preferably an oxygen-binding protein, more preferably hemoglobin, for diffusion enhancement. The composition (solution) comprising the oxygen carrier, preferably hemoglobin, is applied, in case of need, in particular in case of hypoxic need, either before or while gassing, to the peritoneum, and the peritoneal ventilation with an oxygen-comprising gas is performed as known. Surprisingly, it could be shown that transperitoneal oxygenation of mammals, preferably of human beings, can be enhanced by improved oxygen diffusion through the peritoneal fluid to the peritoneum using the liquid composition according to the present invention. On the one hand, this allows in particular local improvement of the oxygenation of the intestinal and gastric walls, as well as of the surfaces of the organs with peritoneum, including in particular abdominal wall, greater omentum, mesentery, urinary bladder, retroperitoneal organs, liver, pancreas, etc.; on the other, this can also be used systemically to increase oxygenation of the entire body via the blood flowing there. Thus, according to the present invention (trans)peritoneal oxygenation is increased both locally and systemically in a simple and effective way by (trans)peritoneal ventilation.

The composition used according to the present invention results in improved peritoneal ventilation. This can therefore be used for a clinically useful method for rescuing patients or promoting their recovery.

This is surprising because, even though it was known before that oxygen carriers such as hemoglobin are capable of reversibly binding oxygen (so-called protein oxygenation) and thus of increasing transport of oxygen in aqueous solutions (mechanism of facilitated diffusion), this diffusion also depends on the nature of the medium to be permeated: Thus, water or aqueous media themselves already constitute diffusion barriers for oxygen, since oxygen is only very poorly soluble in water. Even a thin layer of water is an effective barrier to the transport of oxygen by diffusion. The organs in the abdominal cavity, however, are covered not only with water but with a thin aqueous mucus solution. In healthy human beings, the total volume of this peritoneal fluid amounts to about 50-100 ml. This layer, necessary on the one hand for the mobility of the internal organs, is on the other a significant diffusion barrier for oxygen, inhibiting the passage of oxygen in peritoneal ventilation. All the more surprising was the finding that application of a liquid, likewise diffusion-dependent oxygen-comprising solution improves diffusion of the gaseous oxygen administered in peritoneal ventilation from the abdominal cavity into the tissues (e. g. stomach, intestine, liver).

DETAILED DESCRIPTION OF PREFERRED EMBODIMENTS

According to the present invention, preferably highly concentrated liquid compositions in the form of aqueous solutions, comprising at least one oxygen carrier, preferably an oxygen-binding protein, more preferably hemoglobin, myoglobin, hemocyanin, erythrocruorin, etc., or a derivative thereof produced by chemical modification, or one, or mixtures of several of such oxygen carriers are used as enhancers of the diffusion of oxygen-comprising gas in peritoneal ventilation. According to the present invention, the composition is used in such a manner that the free surface of the organs in the abdominal cavity (the peritoneum) is thinly but as extensively as possible wetted with said solution. To this purpose, devices and methods known per se can be used, as they are for example used for rinsing an abdominal cavity or for subsequent peritoneal ventilation. These basically comprise a flexible or rigid catheter (tube or cannula) and a sharp guide (wire or pin) to pierce the abdominal wall (trocar or sharp stylet).

Replacement of the catheter, e. g. puncture using a rigid one followed by replacement with a flexible catheter, e. g. according to the Seldinger technique, is also possible. The liquid composition comprising the oxygen carrier(s) is injected in this or an analogous manner into the abdominal cavity of the mammal and thus distributed or used to wet the peritoneum. Preferably after that, ventilation with the oxygen-comprising gas is applied. The oxygen-comprising gas is preferably pure oxygen or oxygen-enriched air or an oxygen/inert gas mixture, more preferably a nitrogen-oxygen mixture comprising at least 25% (v/v) oxygen. It can be filled in as an expanded pressurized gas or via suitable pumping devices through the same catheters as the liquid composition according to the present invention. The rate of gas entry is regulated in a manner known per se.

In case of a loss of efficacy of the solution of the diffusion enhancer, this can be re-administered periodically, e. g. every 2 or 4 or 8 hours, etc.

For removal of unnecessary or interfering amounts of aqueous solution in the abdominal cavity, the latter can be flushed and emptied in a known manner using a rinsing solution, before the diffusion enhancer solution is administered again.

This effect of a solution comprising an oxygen carrier such as, preferably, hemoglobin as a diffusion enhancer was not to be expected, since aqueous liquids are essentially, as mentioned before, barriers to the diffusion of oxygen. Surprisingly, however, this can be overcome according to the present invention by applying the composition described above, preferably in a small quantity that results only in wetting of the surface of the peritoneum. For this purpose, the composition of the present invention preferably comprises a high concentration of the oxygen carrier. After mixture with the existing peritoneal fluid, in the resultant layer, which continues to be thin, the additional facilitated diffusion mediated by the oxygen carrier exceeds the additional reduction of simple (free) diffusion of oxygen according to the increased thickness of the mixed aqueous solution.

The present invention is surprising also because it must be assumed that larger quantities of the liquid composition comprising the diffusion-enhancing oxygen carrier may reduce the transfer of oxygen from the ventilation gas to the tissue again, since then the diffusion distances for the oxygen carriers such as hemoglobin would become too long in the then thicker aqueous layer.

1. Components of the Composition Comprising the Oxygen Carriers and their Preparation The liquid composition used according to the present invention is preferably based on water, e. g. purified water for injection, and comprises at least one oxygen carrier (respiratory protein). Combinations of the subsequently listed oxygen carriers are likewise possible. The concentration of the same is preferably equal to or more than 100 g/l. Preferred concentrations are from 150 to 400 g/l, more preferably from 200 to 350 g/l and most preferably from 250 to 300 g/l.

Suitable oxygen carriers are especially those of higher organisms such as hemoglobin, myoglobin, preferably hemoglobin and myoglobin of mammals, more preferably of pigs, humans, cattle, sheep, horses, goats, etc., but also include oxygen transport proteins of lower animals, such as hemocyanins, erythrocruorins, etc.

The oxygen carrier(s) is/are preferably native, i.e. not chemically modified. However, chemically modified derivatives of said oxygen carriers can also be used. The chemical modification can be e. g. a cross-linking, polymerization, covalent addition of another molecule (e. g. a polyalkylene oxide or an effector) or a combination of one or several of these modifications, which is essentially to be understood as including also a further chemical modification not specified here. Crosslinking of monomeric, native or effector-linked hemoglobin or myoglobin using various crosslinking agents is known and described e. g. for divinyl sulphone, epichlorhydrin, butadiene diepoxide, hexamethylene diisocyanate, dialdehydes such as glyoxal and glutaraldehyde, diimide esters such as dimethyl suberimidate, dimethyl malonimidate and dimethyl adipimidate, etc. For pegylation, e. g. polyethylene oxide, polypropylene oxide, or copolymers of ethylene oxide and propylene oxide, preferably esters or ethers thereof, with a short-chain aliphatic organic residue are suitable. A covalently linked polyalkylene oxide or other macromolecule can have a molar mass from 200 to 10,000 g/mol.

Such oxygen carriers and derivatives thereof are known and described for example in DE 100 31 740 A1, DE 100 31 744 A1 and DE 100 31 742 A1, and they can have a molecular weight from 70,000 to 15,000,000 g/mol.

Such methods can be applied to other oxygen carriers as well. The oxygen carrier, preferably hemoglobin or myoglobin, may optionally be deoxygenated by carbonylation for improved shelf life. Preferably the oxygen binding sites of the oxygen carrier are saturated with carbon monoxide, so the agent comprises carbon monoxide. For use, it can optionally be oxygenated, or it is oxygennated in the abdominal cavity by the ventilation gas (within a few minutes). Such carbonylation methods are known.

Most preferably, the oxygen carriers used according to the present invention have an oxygen half-saturation partial pressure p50 from 1 to 50 mmHg. Here the oxygen half-saturation partial pressure p50 is that partial pressure of oxygen at which half of the oxygen carrier molecules have bound oxygen.

Here native hemoglobin or myoglobin of human, porcine or bovine origin are particularly preferred. Such oxygen carriers are preferably carbonylated, as described above.

The preferred amount of oxygen carrier to be used to obtain a maximum diffusion-enhancing effect can be determined according to the quantity determined experimentally by J. B. Wittenberg ("The Molecular Mechanism of Haemoglobin-facilitated Oxygen Diffusion", *Journal of Biological Chemistry* 1966; 241: 104-114) for real, purely aqueous conditions (aqueous solution, hemoglobin). Wittenberg describes a maximum of the facilitated diffusion of $O_2$ through thin layers of aqueous solutions at a hemoglobin concentration of about 100 g/l.

With reference to these empirically determined conditions therefore according to the present invention liquid compositions comprising one or several oxygen carriers for improvement of transperitoneal ventilation in a mammal, preferably a human being, are used at a quantity that will result in a level of said oxygen carriers of about 100 g/l in the peritoneal fluid. The quantity (volume) $V_{HL}$ of the composition solution comprising one (or several) oxygen carrier(s), preferably hemoglobin, that is required to obtain the maximum effect can thus be determined according to the equation:

$$V_{HL}=(100\ g/l \cdot V_{BW})/(c_{HL}-100\ g/l)$$

where $V_{BW}$ is the volume of peritoneal fluid (about 50-100 ml) and $c_{HL}$ the hemoglobin concentration of the hemoglobin solution to be administered.

Hence it follows, for example, that for 50 ml of peritoneal fluid and a concentration of the hemoglobin solution of 400 g/l, 16.7 ml of the latter are required. With 100 ml of peritoneal fluid and a concentration of the hemoglobin solution of 200 g/l, the required quantity is 100 ml. This calculation can be used mutatis mutandis for other oxygen carriers/derivatives as well.

The aqueous composition may furthermore comprise one or more additives selected from salts, preferably from the group consisting of sodium, potassium, calcium and magnesium ions as cations and chloride, (hydrogen) carbonate, (hydrogen) phosphate, citrate and lactate ions as anions, as well as suitable preserving agents, each at a concentration appropriate for the respective application. These are e. g. levels that match those present in the extracellular fluid of the peritoneally ventilated human being (or animal) or approximate them (so-called physiological solutions), or levels of other infusion solutions or solutions for peritoneal lavage or peritoneal dialysis empirically known to be compatible. The pH of the diffusion enhancer solution is adjusted, preferably by titration of the hemoglobin, myoglobin, or other oxygen carrier (respiratory protein), to an appropriate pH value, e. g. from 7.0 to 7.7. The pH of the diffusion enhancer solution according to the present invention is preferably adjusted to a physiological value of about 7.4.

The compositions are prepared using aseptic processes, by extracting the oxygen carrier(s) from their biological sources, purifying it/them and washing it/them out by solvent exchange into one of the aqueous solutions described above. These compositions can then be filled into suitable vials or devices suitable for injection purposes for immediate use.

The invention is also related to a process for preparing a composition for enhancement of oxygen gas, especially of the diffusion of oxygen gas in the peritoneal fluid to improve oxygenation by peritoneal ventilation of a mammal in case of hypoxic need, or for systemic improvement of the oxygenation of a mammal by peritoneal ventilation which process being characterized in that one or more oxygen carriers selected from the group consisting of or a derivate or mixtures thereof are extracted in a manner known per see from biological sources, especially animal blood of the above mentioned animals, purified, optionally chemically modified and subsequently washed out by solvent exchange into one of the aqueous solutions optionally comprising additives, selected from one or more salts, preservatives or mixtures thereof. The pH value is preferably adjusted to a value from 7.0 to 7.7. The pH of the diffusion enhancer solution according to the present invention is Preferably the compositions are immediately filled into suitable vials or devices suitable for injection purposes for immediate use.

Thus the liquid compositions used according to the present invention can be prepared for use for improving peritoneal ventilation, wherein the oxygen carrier(s) is/are present in the indicated concentration, namely from 150 to 400 g/l, preferably from 200 to 350 g/l, more preferably from 250 to 300 g/l, preferably in combination with a physiological sodium chloride content in water.

As oxygen carriers, especially those of higher organisms, such as hemoglobin, are suitable.

Preferred embodiments of the present invention include the following compositions:

compositions comprising, as an oxygen carrier, native or chemically modified hemoglobin or myoglobin of human, bovine, porcine, equine, caprine or ovine origin, or mixtures thereof, in an aqueous salt solution, preferably sodium chloride solution, for introduction into the abdominal cavity and distribution over/wetting of the organs of the abdominal cavity;

compositions with an isotonic solution with native porcine hemoglobin;

compositions with native or chemically modified hemocyanin or erythrocruorin of a lower animal in an aqueous salt solution, preferably sodium chloride solution, for introduction into the abdominal cavity and distribution over/wetting of the organs of the abdominal cavity;

compositions wherein the concentration of the oxygen carrier used in the aqueous solution is from 150 to 400 g/l, preferably from 200 to 350 g/l and most preferably from 250 to 300 g/l;

compositions comprising one or several oxygen carriers whose oxygen binding sites are saturated, for improved shelf life, prior to use with carbon monoxide, so that the agent comprises carbon monoxide.

compositions comprising, as an oxygen carrier, native or chemically modified hemocyanin in an aqueous salt solution, preferably sodium chloride solution;

compositions comprising native or chemically modified erythrocruorin or a chemically modified derivative thereof in an aqueous salt solution, preferably sodium chloride solution.

2. Administration and Application of the Composition

The composition used according to the present invention is preferably introduced into the abdominal cavity by means of suitable injection devices prior to gassing.

The preferred injection rate of the liquid composition depends on the configuration of the catheter; the liquid jet must not injure the abdominal organs. For example, about 100-200 ml/min appear expedient. The liquid composition is administered from conventional reservoirs, e. g. a syringe, infusion bottle, infusion bag, etc.; according to the present invention preferably the abdominal cavity is first filled or wetted, respectively, with a defined quantity of the liquid composition and then charged with a defined quantity of gas.

The gassing of the abdominal cavity is known, and various equipment items and procedures are described in the literature listed below:

Barr J., et al.: "Peritoneal Ventilation: An Animal Model of Extrapulmonary Ventilation in Experimental Adult Respiratory Distress Syndrome", *Pediatric Research* 1994; 35: 682-284;

Zhang J.-Y., et al.: "Effect of Oxygenation of Transperitoneal Ventilation on the Death Time after Asphyxiation in Rabbits", *Minerva Anesthesiologica* 2010; 76: 913-918;

Giffin D. M., et al.: "Oxygen Uptake during Peritoneal Ventilation in a Porcine Model of Hypoxemia", *Critical Care Medicine* 1998; 26: 1564-1568;

Wang X., et al.: "The Effect of High and Conventional Frequency Peritoneal Jet Ventilation on Hypoxemia in ARDS Dogs", *European Journal of Anaesthesiology* 2012; 29: 180.

The injected oxygen carrier, especially the administered hemoglobin, preferably native hemoglobin of human, porcine or bovine origin, can be removed again at least predominantly by flushing the abdominal cavity with a rinsing solution. This is done via the said catheters. As the rinsing solution, preferably a known isotonic aqueous rinsing solution is used. Thus, the abdominal cavity can be purified again after peritoneal ventilation. Removal of hemoglobin may become necessary also e. g. to renew the oxygen carrier, preferably hemoglobin. For gradual oxidation of hemoglobin also in an abdominal cavity to methemoglobin (hemiglobin), which is no longer able to bind oxygen, is likely. Suitable systems and devices for reducing to practice the present invention are familiar from the state of the art, in particular from dialysis technology (peritoneal emergency dialysis).

The previously described aqueous composition comprising an oxygen carrier, preferably having an oxygen half-saturation partial pressure of 1 to 50 mmHg, is therefore suitable for the application and use to enhance the diffusion of oxygen (gas) applied to mucus layers on the peritoneum, and in particular for the wetting of the abdominal cavity in peritoneal ventilation for improvement of oxygen diffusion through the mucus layer on the peritoneum.

The application can be as follows:

i) Provision of an aqueous composition comprising at least one oxygen carrier, preferably selected from hemoglobin, myoglobin, hemocyanin and erythrocruorin, in native form or in the form of derivatives that are cross-linked, pegylated, polymerized, or otherwise chemically derivatized or carbonylated in a known manner, or mixtures thereof, as described above;

ii) injection of said composition into the abdominal cavity at a quantity and rate appropriate for the application, as explained above;

iii) gassing of the abdominal cavity in a manner known per se with an oxygen-comprising gas such as air or nitrogen, comprising 25 to 100% (v/v) of oxygen;

iv) possibly removal of excess composition according to i) and/or flushing of the abdominal cavity with a rinsing solution, e. g. isotonic saline.

3. Indications for the Composition Used According to the Present Invention

The composition is especially suitable for improving the oxygenation of a mammal by peritoneal ventilation in case of hypoxia induced by pulmonary failure due to a bacterial or viral infection, to corrosive injury, to circulatory shock, such as hemorrhagic or septic shock, to trauma or to intoxication as e. g. in case of smoke inhalation, to pulmonary embolism or to pneumonia of any genesis.

It can also be used for local oxygenation of individual organs adjacent to the abdominal cavity and at least partially covered with peritoneum, such as intestines, stomach, pancreas and liver in case of relevant need, or in case of (relative or absolute) oxygen deficiency due to reduced perfusion (local hypoxia), e. g. in case of local vascular occlusion (infarction resulting from thrombosis or embolism, e. g. bowel infarction), or a blood flow distribution disorder, e. g. due to circulatory shock. Furthermore, the composition according to the present invention can also be useful for increasing the oxygenation of organs in the abdomen treated with cells or similar, e. g. upon implantation of insulin-producing Langerhans cells into the liver, etc.

As patients, preferably humans, horses, camels, dogs, cats, cattle, or other mammals in a condition of need as described herein are eligible. The composition used according to the present invention preferably relates to human beings.

EXAMPLES

Example 1—Preparation of a Composition According to the Present Invention with Native Porcine Hemoglobin Porcine hemoglobin was obtained from fresh blood of slaughtered domestic pigs and purified: Per liter of porcine whole blood, 5 ml of phenoxyethanol and 4 g of sodium citrate were added and mixed. By centrifugation (12 min·3, 800 g), the plasma was separated and removed by aspiration. Twice the erythrocytes were suspended in saline (9.0 g/l), centrifuged again, and the supernatant was aspirated. By addition of water (2.5 l/l), the erythrocytes were lysed; by addition of crystalline sodium chloride (9.0 g/l) and stirring, an isotonic medium was re-established, by addition of NaOH the pH was adjusted to 7.0, and by stirring under CO gas and bubbling of the gas through the hemoglobin solution the hemoglobin was fully carbonylated. By heating to 75° C., residues of erythrocyte membranes were removed by aggregation; centrifugation (12 min·3,800 g) and subsequent filtration clarified the supernatant. Then by dialysing ultra-filtration the medium was extensively (2.5 l/l) replaced with a 9.0 g/l NaCl solution, and by pure tangential flow ultra-filtration finally the hemoglobin solution was concentrated.

To refresh the carbonylation, the solution was again equilibrated with CO gas (by shaking of a container half filled with each of solution and CO gas).
The following composition was obtained:
Hemoglobin concentration: 350 g/l
NaCl concentration: 9.0 g/l
Carbon monoxide concentration: ≤1.02 mmol/l (=solubility in the solvent)
Osmolarity (calculated): 309 mosmol/l
pH: 7.1
Base: Water This solution is suitable for use as a composition according to the present invention and to effect the improvement of oxygen uptake by peritoneal ventilation according to the present invention.

Example 2—Preparation of Cross-Linked Porcine Hemoglobin

Highly purified porcine hemoglobin, dissolved at a concentration of 330 g/l in an aqueous electrolyte comprising 50 mM of $NaHCO_3$ and 100 mM of NaCl, was deoxygenated at 4° C. by stirring the solution under constantly renewed pure nitrogen over the solution. Subsequently, 4 mol of sodium ascorbate (as a 1 M solution in water) per mol of (monomeric) hemoglobin were added and allowed to react for 6 h. The solution was titrated with 0.5 M lactic acid to a pH of 7.1, then 1.1 mol of pyridoxal-5'-phosphate per mol of hemoglobin were added and allowed to react for 16 h. Now using 0.5 M sodium hydroxide solution the pH was adjusted to 7.8; then 1.1 mol of sodium borohydride were added (as a 1 M solution in 0.01 M sodium hydroxide solution) and allowed to react for one hour. Next the pH was adjusted to 7.3 with 0.5 M lactic acid; then initially 1.1 mol of 2,3-bisphosphoglycerate per mol of hemoglobin and, after 15 min of reaction time, 8 mol of glutaraldehyde per mol of hemoglobin, dissolved in 1.8 l of pure water per liter of hemoglobin solution were added within 5 min for crosslinking of the hemoglobin and allowed to react for 2.5 h. After titration with 0.5 M sodium hydroxide to a pH of 7.8, addition of 15 mol of sodium borohydride (as a 1 M solution in 0.01 M sodium hydroxide) per mol of hemoglobin for 1 h followed. Addition of 2 liters of water per liter of original hemoglobin solution followed. The pH was then 9.3, and addition of 4 mol methoxysuccimidyl propionate polyethylene glycol having a molecular weight of 2,000 g/mol for 2 h immediately followed. The nitrogen atmosphere over the solution was replaced by pure oxygen.

After 1 h, insoluble components were removed by centrifugation (20,000 g for 15 min). Subsequently, by volume exclusion chromatography (Sephadex G-25 gel, Pharmacia, D) the electrolyte was replaced with an aqueous electrolyte solution of 125 mM NaCl, 4.5 mM KCl and 20 mM $NaHCO_3$.

The yield for soluble polymerized hemoglobin was 77%, the yield for polymers with molecular weights greater than 700,000 g/mol was 28%.

The methemoglobin fraction was less than 5%; measurements of the characteristics of the oxygen binding under physiological conditions (at a temperature of 37° C., a carbon dioxide partial pressure of 40 mmHg and a pH of 7.4) showed a p50 value of 22 mmHg and an n50 value of 1.95 for the product.

This cross-linked porcine hemoglobin is suitable to be used in a composition according to the present invention for improvement of oxygen uptake by peritoneal ventilation.

In analogy to the above examples, compositions according to the present invention comprising native or cross-linked myoglobin according to Examples 1 and 2 or hemocyanin (native) at the given preferred concentration of 150 to 400 g/l can likewise be prepared and applied.

Example 3—Improvement of Peritoneal Ventilation

Improved tissue oxygenation by peritoneal ventilation according to the invention is demonstrated as an improved oxygenation of the ileum in a rat septic shock model using a formulation according to example 1.

In ventilated narcotized rats (with body weights of about 300 g) a septic shock was induced by IV injection of LPS (lipopolysaccharide, about 3 mg/kg) from *Escherichia coli*. 3 hours later the animals were narcotized with isoflurane inhalation. To obtain and maintain a stable systemic blood pressure of approximately 90 mmHg the animals got an IV infusion of norepinephrine (from 0.01 to 10 mg $kg^{-1}$ $min^{-1}$ as required). A reflexion spectrometer O2C (LEA Medizintechnik, Giessen, Germany) was used to determine the oxygenation of the ileal mucosa. (esp. as the capillary-venulous oxygen saturation of hemoglobin in the blood of this tissue) which served as a measure of efficiency of the peritoneal ventilation. The measuring probe was mounted onto the ileum and fixed in this position.

In order to demonstrate the improvement of oxygenation of the ileum according to the invention, the abdominal serosa of the animals was coated either with 0.5 mL isotonic NaCl solution (control group) or with 0.5 mL of an aqueous solution of 20% porcine hemoglobin in isotonic NaCl (intervention group) followed by a slow perfusion of pure (humidified) oxygen gas (99.5%, about 5 mL/min) through the abdominal cavity in all animals.

Animals treated with the hemoglobin solution and oxygen perfusion exhibited a higher blood oxygen saturation in their ileum in comparison to the control group.

What is claimed is:
1. A method for enhancing diffusion of oxygen gas during the performing of a peritoneal ventilation said peritoneal ventilation with gasiform oxygen-containing gases and comprising transperitoneal administration of oxygen from a purely gasiform gas introduced directly into the abdominal cavity comprising the steps of:
   i) providing an aqueous composition comprising at least one oxygen-binding protein (oxygen carrier), selected from hemoglobin, myoglobin, hemocyanin, erythrocruorin, in native form or in the form of derivatives that are cross-linked, pegylated, polymerized, or otherwise chemically derivatized or carbonylated, or mixtures thereof;
   ii) introducing said aqueous composition into an abdominal cavity at a quantity and rate appropriate for the application; and
   iii) gassing of the abdominal cavity with an oxygen comprising gas, selected from air, an oxygen/inert gas mixture, or pure oxygen.
2. The method according to claim 1, wherein the step of preparing an aqueous composition comprises preparing an aqueous composition which comprises native porcine hemoglobin with an oxygen half-saturation partial pressure between 1 and 50 mmHg.

3. The method according to claim 1, wherein the aqueous composition comprising an oxygen-binding protein (oxygen carrier) comprises native or chemically modified hemoglobin or myoglobin of human, bovine, porcine, equine, caprine or bovine origin, or mixtures thereof in an aqueous salt solution; and further comprising the steps of:
    introducing the aqueous composition into an abdominal cavity;
    distributing the aqueous composition between the organs of the abdominal cavity; and
    wetting a surface of the organs.

4. The method according to claim 1, wherein the aqueous composition comprising an oxygen-binding protein (oxygen carrier) comprises native hemoglobin of porcine origin, in an isotonic solution.

5. The method according to claim 1, wherein the aqueous composition comprising an oxygen-binding protein (oxygen carrier) comprises a composition with native or chemically modified hemocyanin or erythrocruorin of a lower animal in an aqueous salt solution; and further comprising the steps of:
    introducing the aqueous composition into an abdominal cavity;
    distributing the aqueous composition over the organs of the abdominal cavity; and
    wetting a surface of the organs.

6. The method according to claim 5, wherein the aqueous salt solution is aqueous sodium chloride solution.

7. The method according to claim 1, wherein a concentration of the oxygen carrier especially the oxygen binding protein in the aqueous solution is from 150 to 400 g/l.

8. The method according to claim 1, wherein at least one oxygen binding protein (oxygen carrier) is used whose oxygen binding sites are saturated, for improved shelf life, prior to use with carbon monoxide, so that the at least one oxygen binding protein becomes saturated with carbon monoxide.

9. The method according to claim 1, wherein the ii) introducing is by injection.

10. The method according to claim 1, wherein the oxygen-binding protein is cross-linked with a crosslinking agent selected from the group consisting of divinyl sulphone, epichlorhydrin, butadiene diepoxide, hexamethylene diisocyanate, a dialdehyde, glyoxal, glutaraldehyde, a diimide ester, dimethyl suberimidate, dimethyl malonimidate and dimethyl adipimidate.

* * * * *